United States Patent
Lee et al.

(10) Patent No.: US 7,465,828 B2
(45) Date of Patent: Dec. 16, 2008

(54) METHOD FOR PREPARING HYDRAZODICARBONAMIDE USING BIURET AS STARTING MATERIAL

(75) Inventors: Chun-Hyuk Lee, Kyonggi-Do (KR); Sang-Jin Han, Kyonggi-Do (KR)

(73) Assignee: J&J Chemical Co., Ltd. (KR)

( * ) Notice: Subject to any disclaimer, the term of this patent is extended or adjusted under 35 U.S.C. 154(b) by 194 days.

(21) Appl. No.: 11/015,853

(22) Filed: Dec. 17, 2004

(65) Prior Publication Data

US 2005/0107566 A1    May 19, 2005

Related U.S. Application Data

(63) Continuation of application No. PCT/KR02/01862, filed on Oct. 7, 2002.

(30) Foreign Application Priority Data

Jun. 17, 2002    (KR) .......................... 2002-0033814

(51) Int. Cl.
    *C07C 281/06*    (2006.01)
(52) U.S. Cl. .......................... 564/35; 564/34
(58) Field of Classification Search .............. 564/35, 564/34; 528/68
    See application file for complete search history.

(56) References Cited

U.S. PATENT DOCUMENTS 6,635,785 B1 * 10/2003 Lee et al. .................... 564/35
2004/0199012 A1   10/2004 Lee et al. .................... 564/35

FOREIGN PATENT DOCUMENTS

KR        2001-68668        7/2001

OTHER PUBLICATIONS

Morrison, Robert, and Boyd, Robert. "Organic Chemistry. 3rd Edition." Boston: Allyn and Bacon, Inc. 1966.*
International Preliminary Examination Report dated Sep. 30, 2004.

* cited by examiner

*Primary Examiner*—Rabon Sergent
*Assistant Examiner*—Benjamin Gillespie
(74) *Attorney, Agent, or Firm*—Park & Associates IP Law LLP

(57) ABSTRACT

The method for preparing hydrazodicarbonamide (HDCA) using biuret as a starting material is disclosed. The method comprises the steps of; obtaining metal monohalobiuret salt by reacting a biuret with a metal hypohalogen compound, or by reacting the biuret with a halogenating agent and a base; and reacting the obtained metal monohalobiuret salt with ammonia, wherein the hydrazodicarbonamide is produced in the presence of a catalyst including bromine or iodine atom and generating bromine or iodine ion during the reaction.

9 Claims, No Drawings

METHOD FOR PREPARING HYDRAZODICARBONAMIDE USING BIURET AS STARTING MATERIAL

This application is a continuation of pending International Patent Application No. PCT/KR02/01862 filed Oct. 7, 2002 which designates the United States and claims priority of pending Korean Patent Application No. 2002-33814 filed Jun. 17, 2002.

BACKGROUND OF THE INVENTION

1. Field of the Invention

The present invention relates to a method for preparing hydrazodicarbonamide (HDCA) using biuret as a starting material, and more particularly, to a more economical and efficient method for preparing HDCA than the method described in Korean Patent application No. 2000-691 of the present inventors.

2. Backgrounds of the Invention

Hydrazodicarbonamide (HDCA) is a useful compound as a source material for producing azodicarbonamide which is one of the world-widely used foaming agents. As shown in the following Reaction equation 1, azodicarbonamide (2) can be obtained by oxidizing hydrazodicarbonamide (1) with an appropriate oxidizing agent.

[Reaction equation 1]

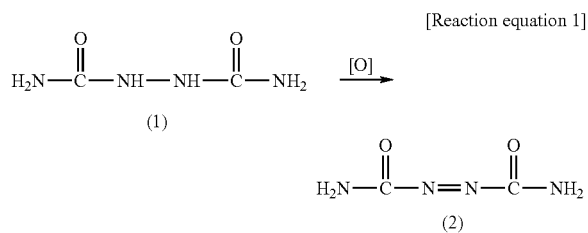

Conventional methods for preparing HDCA includes (i) a method of reacting 2 moles of urea with hydrazine which is produced by Raschig process or derived from ketazine, (ii) a method of reacting 2 moles of urea with hydrazine which is derived from urea (Urea Process), (iii) a method of reacting 1 mole of urea with semicarbazide which is produced by reacting sodium hypochlorite, urea and ammonia, and (iv) a method of using biuret as a starting material. However, the methods (i) and (iii) which use hydrazine or semicarbazide and the method (ii) have drawbacks such as a complicated reaction process, a low yield, a high raw material cost, and a long reaction time. Furthermore, the above-described methods are environmentally undesirable since the large quantities of the raw materials are required to produce HDCA.

To overcome these drawbacks, the present inventors have proposed a method for synthesizing HDCA using biuret as a starting material (See Korean Patent application No. 2000-691), and the method is shown in the following Reaction equation 2.

[Reaction equation 2]

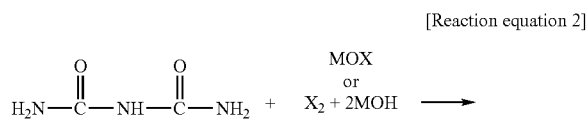

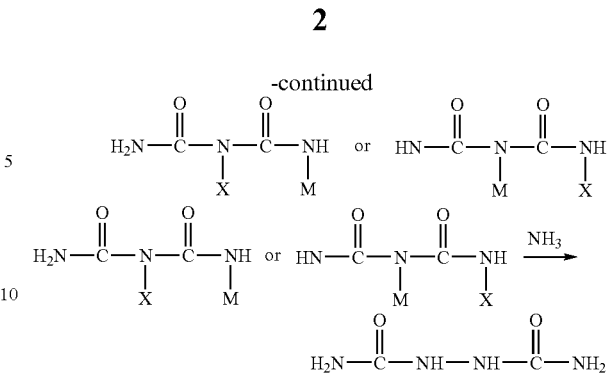

wherein, M is a metal and X is a halogen. As shown in reaction equation 2, Korean Patent application No. 2000-691 discloses the method for preparing HDCA comprising the steps of (i) reacting biuret with metal hypohalogen or halogen/base to obtain metal monohalobiuret salt, and (ii) reacting the obtained metal monohalobiuret salt with ammonia to produce HDCA. However, in order to produce HDCA in industrially preferable yield with the above described method, a metal compound catalyst such as sulfates, chlorides, carbonates or hydroxides of amphoteric metal or alkali metal, or an inorganic acid catalyst such as hydrochloric acid, sulfuric acid or nitric acid are required in the amount of more than 0.05 moles with respect to 1 mole of monohalobiuret. Therefore, this method has drawbacks in that it requires high catalyst cost and the cost for after-treatment of the produced HDCA due to the large amount of the residual catalyst, and the method is also environmentally undesirable. In addition, the reaction rate and yield are not sufficiently high even when these catalysts are used.

SUMMARY OF THE INVENTION

It is an object of the present invention to provide the method for preparing hydrazodicarbonamide preferable in economical and environmental aspects.

It is other object of the present invention to provide the method for preparing hydrazodicarbonamide, which can decrease the reaction time and increase the yield of the reaction.

It is another object of the present invention to provide the method for preparing hydrazodicarbonamide, which can reduce the amounts of the raw material such as ammonia and catalyst.

In order to achieve these objects, the present invention provides a method for preparing hydrazodicarbonamide in the presence of a catalyst including bromine or iodine atom and generating bromine or iodine ion during the reaction, and the methods comprises the steps of: obtaining metal monohalobiuret salt having formula 2 or 3 by reacting a biuret having the formula 1 with a metal hypohalogen compound, or by reacting the biuret having formula 1 with a halogenating agent and a base; and reacting the obtained metal monohalobiuret salt with ammonia.

[Formula 1]

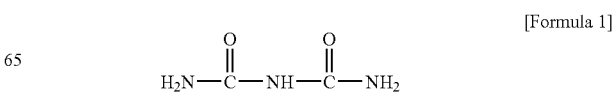

[Formula 2]

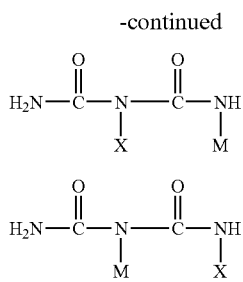

[Formula 3]

Preferably, the metal monohalobiuret salt is produced by reacting the biuret having formula 1 with a halogenating agent to obtain a monohalobiuret having the formula 4 or 5, and then by reacting the obtained monohalobiuret with a base.

[Formula 4]

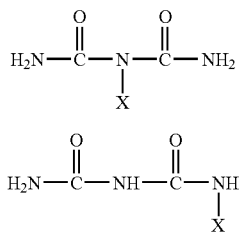

[Formula 5]

In the above formulas 2 to 5, M is a metal, and X is a halogen.

Also preferably, the catalyst can be a brominating agent or iodinating agent such as metal bromide, metal iodide, brominated organic compound, iodinated organic compound or the mixtures thereof. The more preferable catalyst includes NaBr, KBr, KI, $CuBr_2$, CuI, HBr, HI, $PBr_3$, $Br_2$, $I_2$, N-bromosuccinimide or the mixtures thereof. The catalyst can be added for the reaction, before, during or after the reaction of biuret with metal hypohalogen compound or with a halogenating agent and a base, and more preferably added for the reaction before the reaction of biuret with metal hypohalogen compound or with a halogenating agent and a base. The preferable amount of the catalyst is 0.001 to 1 mole, and more preferably 0.002 to 0.5 moles with respect to 1 mole of the monohalobiuret and/or metal monohalobiuret salt.

DETAILED DESCRIPTION OF THE INVENTION

A more complete appreciation of the invention, and many of advantages thereof, will be readily apparent, as the same becomes better understood by reference to the following detailed description.

The method of preparing metal monohalobiuret salt having the formula 2 or 3 by reacting biuret with metal hypohalogen compound according to the present invention is shown in the following reaction equation 3, and the specific example is shown in the following Reaction equation 4.

[Reaction equation 3]

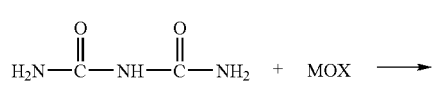

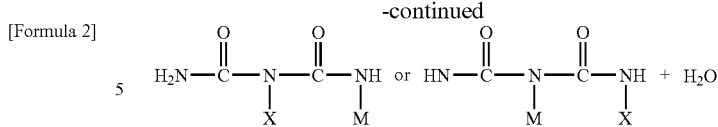

In the above Equation, M is a metal, and X is a halogen.

[Reaction equation 4]

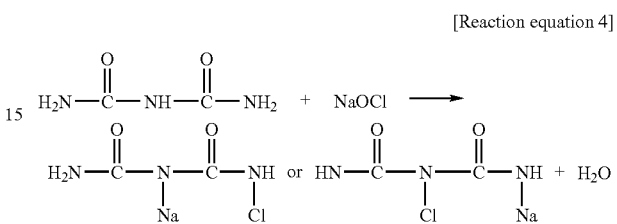

Referring to Equation 4, biuret reacts with sodium hypochlorite to produce sodium chlorobiuret salt. Since the above reaction is an exothermic reaction, it is preferable that the reaction system is maintained at low temperature. However, the produced sodium chlorobiuret salt is relatively stable to heat. Therefore the reaction can be carried out at room temperature. Preferable reaction temperature is less than 60 C more preferably −10 C to 60 C, and most preferably −5 C to 35 C Considering the economical efficiency and operational facility, the preferable mol ratio of metal hypohalogen per 1 mol of biuret is 0.1 to 2 moles. If less than 1 mole of metal hypohalogen is used for 1 mol of biuret, the excess biuret can be recovered and reused. In above reaction, when the mole ratio of metal hypohalogen is less than 0.1 mole or the reaction temperature is less than −10 C, the reaction time may be too long. And if the mole ratio is more than 2, the production cost may increase and side reactions may occur. If the reaction temperature is more than 60 C, the produced metal monohalobiuret salt may be decomposed because the compound is unstable at high temperature. Sodium chlorobiuret salt obtained under aforementioned conditions can be used directly for subsequent reaction in continuous process, or can be stored for next reaction in batch process.

An exemplary process of obtaining metal monohalobiuret salt having the formula 2 or 3 by reacting biuret with a halogenating agent and a base is shown in the following Reaction equation 5. As shown in Equation 5, after reacting biuret with a halogenating agent such as halogen ($X_2$) to obtain monohalobiuret 5, a base, for example, a metal hydroxide such as sodium hydroxide, calcium hydroxide or potassium hydroxide are added to produce metal monohalobiuret salt.

[Reation equation 5]

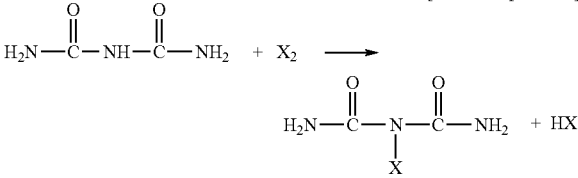

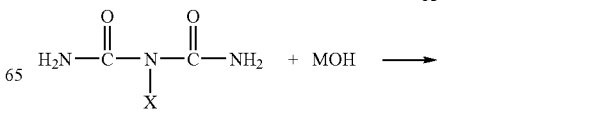

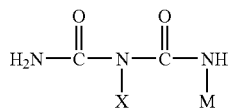

In the above reaction equation, M is a metal, and X is a halogen.

In the above reaction, considering that the halogenating reaction is an exothermic reaction, it would be advantageous that the reaction temperature is maintained lower, specifically less than 60 C, preferably within the range of −10 C to 60 C, more preferably within the range of −5 C to 30 C for proper reaction rate and the stability of the reaction. Alternatively, metal monohalobiuret salt can be obtained by reacting metal hydroxide with biuret at first, and then reacting the obtained product with a halogenating agent. Since the alternative reaction is also an exothermic reaction, the reaction temperature should be maintained lower, specifically within the range of −10 C to 60 C, more preferably within the range of −5 C to 30 C If the reaction temperature is less than −10 C, the reaction time may be too long, and if the reaction temperature is more than 60 C, the produced metal monohalobiuret salt may be decomposed because the compound is unstable at high temperature.

In summary, metal 3-monohalobiuret salt or metal 1-monohalobiuret salt is obtained from biuret as shown in the following Reaction equation 6.

[Reaction equation 6]

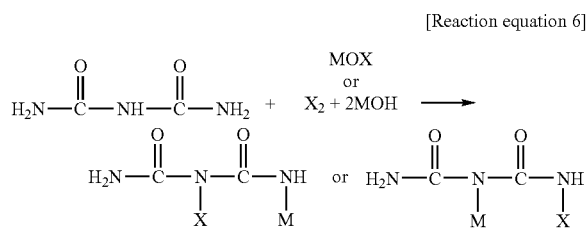

The obtained metal monohalobiuret salt reacts with ammonia to produce hydrazodicarbonamide (HDCA). The reaction mechanism is presumed to be similar to Favorskii reaction shown in Reaction equation 7 or Hofmann rearrangement reaction shown in Reaction equation 8.

[Reaction 7]

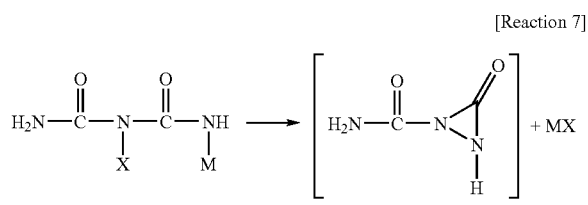

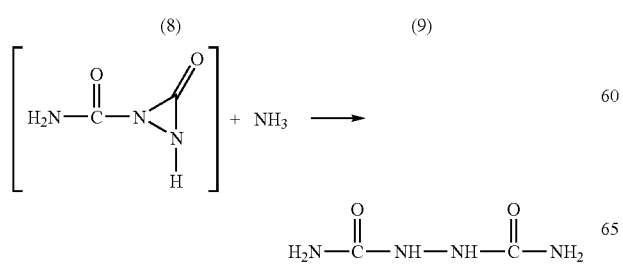

[Reaction 8]

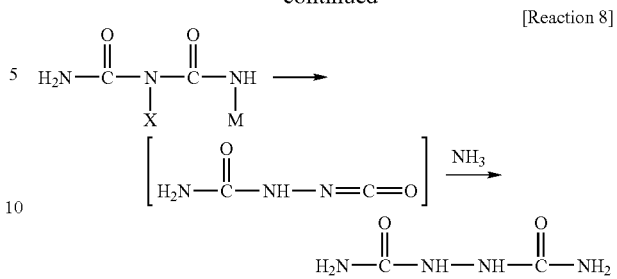

Referring to the above Reaction equation 7, by the intermolecular reaction of anionic nitrogen atom in metal monohalobiuret salt, a metal halogen(MX) compound is eliminated from metal monohalobiuret salt, and N—N bond is formed to produce an unstable diaziridinone derivative 9. The produced diaziridinone derivative immediately reacts with highly reactive ammonia to give HDCA. Referring to the above Reaction equation 8, metal monohalobiuret salt is converted into an isocyanate compound, and the converted isocyanate compound can reacts with highly reactive ammonia to produce HDCA.

According to the present invention, HDCA is produced in the presence of a catalyst including bromine or iodine atom and generating bromine or iodine ion during the reaction. Examples of the catalyst include a brominating agent or iodinating agent such as metal bromide or metal iodide (for example, NaBr, KBr, KI, $CuBr_2$, CuI), hydrogen halide (for example, HBr, HI), a compound generating a halogen ion (for example, $Br_2$, $I_2$, $PBr_3$), and halogenated organic compound (for example, N-bromosuccinimide: NBS). The preferable amount of the catalyst is 0.001 to 1 mole, and more preferably 0.002 to 0.5 moles with respect to 1 mole of the monohalobiuret and/or metal monohalobiuret salt. If the amount of the catalyst is less than 0.001 mole, the reaction yield and the reaction rate may decrease, and if the amount of the catalyst is more than 1 mole, there are no additional preferable effects and it is just disadvantageous in economical aspect.

By using the catalyst, the reaction yield and the reaction rate can be improved and the required amount of ammonia can be reduced. This seems that the catalyst accelerates the formation of diaziridinone derivative or Hoffmann rearrangement reaction. As a specific example, if sodium monochlorobiuret salt is produced by reacting sodium hypochlorite (NaOCl) and biuret, chlorine ion of sodium monochlorobiuret salt can be replaced by bromine or iodine ion of the catalyst to give sodium monobromobiuret salt or sodium monoiodobiuret salt which is a more reactive intermediate. This reaction is shown in the following Reaction equations 9 and 10.

[Reaction equation 9]

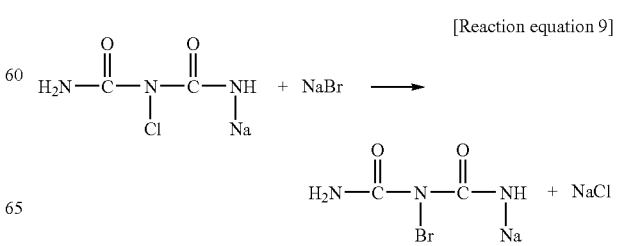

-continued

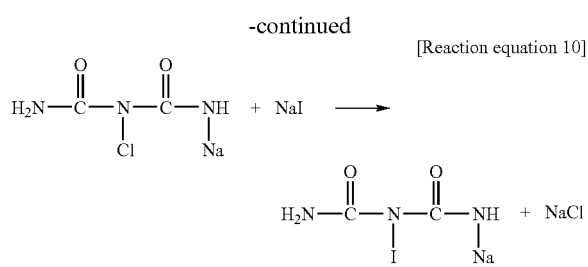

[Reaction equation 10]

These catalysts not only increase yield of metal monohalobiuret salt by inhibiting side reactions but also contribute significantly to improve the yield, to reduce the reaction time and to reduce the required amount of ammonia by accelerating the reaction of monohalobiuret and ammonia. The catalyst may be added for the reaction, before, during or after the reaction of biuret with metal hypohalogen compound or with a halogenating agent and a base, and more preferably added for the reaction before the reaction of biuret with metal hypohalogen compound or with a halogenating agent and a base.

Considering the reaction rate and efficiency of the reaction of metal monohalobiuret salt and ammonia, the preferable reaction temperature is in the range of 0 C to 150 C, more preferably 30 C to 150 C If the reaction temperature is less than 0 C, it is uneconomical due to a very low reaction rate, and if the temperature is more than 150 C, expensive equipment is required to cope with the internal pressure elevation due to the evaporation of ammonia. Ammonia can be used in either form of gaseous ammonia, liquid ammonia or ammonium hydrate. Ammonia can be used in excess amount to increase the reaction rate. Specifically, the preferable amount of ammonia is 1 to 1000 moles, more preferably 2 to 500 moles, and most preferably 5 to 100 moles with respect to 1 mole of metal monohalobiuret salt. The excess ammonia not reacting with metal monohalobiuret salt can be recovered and reused. If excess ammonia is used and the reaction temperature is high, the reaction can be carried out under pressure in order to increase the reaction rate and efficiency by preventing the evaporation of ammonia, and the preferable range of the pressure is between 1 to 100 kgf/cm$^2$.

As a solvent for biuret or the reaction system, water can be used. Alternatively, a hydrophobic organic solvent (the second solvent) can be used as the solvent for the reaction, and a mixture of hydrophobic organic solvent and water can also be used as the solvent. Examples of the hydrophobic organic solvent include chlorinated hydrocarbon such as methylchloride, aliphatic hydrocarbon such as hexane, aromatic hydrocarbon such as toluene and benzene, acetate such as ethylacetate, and ether. If the hydrophobic organic solvent is used along with water, monohalobiuret produced by reaction of biuret and a halogenating agent is dissolved into the hydrophobic organic solvent. In this case, the second solvent can be separated from water by phase separation for the subsequent reaction with base and/or ammonia. This process further prevents side reactions, increases the yield of HDCA, and decreases the amount of waste water.

More than one of the hydrophobic organic solvent can be mixed with water, and the amount of the hydrophobic organic solvent is not limited, but preferably 0.1 to 50 times, and more preferably 0.2 to 3.0 times of water by weight. The organic solvent may be added at the beginning of the reaction as a solvent for biuret, or added after monohalobiuret is synthesized.

Hereinafter, the preferable examples and manufacturing examples are provided for better understanding of the present invention. However, the present invention should not be restricted to the following Examples. All of the following examples and manufacturing examples are carried out by batch process, but continuous process can also be employed.

MANUFACTURING EXAMPLE 1

Synthesis of Sodium Chlorobiuret Salt 423.1 g (0.287 moles) of 7% biuret slurry solution was added into a 2 L glass reactor, and the temperature of the reaction system was maintained at 5 C or less. 0.3 g (0.0029 moles) of NaBr as a catalyst was added into the reactor, 170 g (0.287 moles) of a 12% aqueous solution of sodium hypochlorite was added, and the temperature of the reaction system was maintained at 5 C or less. After completion of the addition, the reaction solution was analyzed by iodometry and liquid chromatography. The available chlorine of the reaction solution was 3.40% and the yield was 99%.

MANUFACTURING EXAMPLE 2

Synthesis of Sodium Chlorobiuret Salt 423.1 g (0.287 moles) of a 7% biuret slurry solution was added into a 2 L glass reactor, and the temperature of the reaction system was maintained at 5 C or less. 0.3 g (0.0029 moles) of NaBr as a catalyst was added into the reactor, 223 g (0.575 moles) of a 10.3% aqueous solution of sodium hydroxide was added, and 20.3 g (0.287 moles) of chlorine gas was added while maintaining the temperature of the reaction system at 10 C or less. After completion of the addition, the reaction solution was analyzed by iodometry and liquid chromatography. The available chlorine of the reaction solution was 3.01% and the yield was 99%.

MANUFACTURING EXAMPLE 3

Synthesis of Sodium Chlorobiuret Salt 423.1 g (0.287 moles) of a 7% biuret slurry solution was added into a 2 L glass reactor, and the temperature of the reaction system was maintained at 5 C or less. 0.3 g (0.0029 moles) of NaBr as a catalyst was added into the reactor, 20.3 g (0.287 moles) of chlorine gas was added while maintaining the temperature of the reaction system at 10 C or less. After the addition of chlorine gas, 223 g (0.575 moles) of a 10.3% aqueous solution of sodium hydroxide was added while vigorously stirring, and the reaction temperature was maintained at 5 C or less. After completion of the addition, the reaction solution was analyzed by iodometry and liquid chromatography. The available chlorine of the reaction solution was 3.01% and the yield was 99%.

EXAMPLES 1-9

Synthesis of Hydrazodicarbonamide (HDCA)

593.1 g of the sodium chlorobiuret salt prepared according to the manufacturing example 1 was added into a 2 L autoclave, and cooled to 10 C while stirring. After adding 600 g (8.8 moles) of 25% aqueous ammonia solution while maintaining the temperature of the reaction solution at 10 C or less, the reactions were carried out by varying the reactor temperatures and the reaction times while vigorously stirring the reaction solution. After completion of the reaction, unreacted ammonia was removed and the reaction solution was filtered. The yield of water insoluble HDCA was calculated and shown in the following Table 1.

TABLE 1

| Example | Reaction conditions (temperature, time) | Yield (%) |
| --- | --- | --- |
| 1 | 30 C., 1 hour | 91 |
| 2 | 30 C., 2 hours | 98 |
| 3 | 30 C., 3 hours | 98 |
| 4 | 60 C., 30 minutes | 98 |
| 5 | 60 C., 1 hour | 97 |
| 6 | 60 C., 2 hours | 97 |
| 7 | 90 C., 30 minutes | 95 |
| 8 | 90 C., 1 hour | 94 |
| 9 | 90 C., 2 hours | 94 |

EXAMPLES 10-16

Synthesis of Hydrazodicarbonamide (HDCA)

Except that each 0.0029 mole of the catalysts shown in the following Table 2 was used instead of NaBr, the reactions were carried out according to the same method of Example 4. After completion of the reaction, unreacted ammonia was removed and the reaction solution was filtered. The yield of water insoluble HDCA was calculated and shown in the following Table 2.

TABLE 2

| Example | The used catalyst | Yield (%) |
| --- | --- | --- |
| 10 | KBr | 95 |
| 11 | KI | 94 |
| 12 | N-bromosuccinimide (NBS) | 95 |
| 13 | HBr | 97 |
| 14 | PBr$_3$ | 97 |
| 15 | ZnBr$_2$ | 97 |
| 16 | CuBr$_2$ | 95 |

EXAMPLE 17-25

Synthesis of Hydrazodicarbonamide (HDCA)

666.7 g of the chlorobiuret sodium salt prepared according to the manufacturing example 2 was added into a 2 L autoclave, and cooled to 10 C while stirring. After adding 600 g (8.8 moles) of 25% aqueous ammonia solution while maintaining the temperature of the reaction solution at 10□ or less, the reactions were carried out by varying the reactor temperatures and the reaction times while vigorously stirring the reaction solution. After completion of the reaction, unreacted ammonia was removed and the reaction solution was filtered. The yield of water insoluble HDCA was calculated and shown in the following Table 3.

TABLE 3

| Example | Reaction conditions (temperature, time) | Yield (%) |
| --- | --- | --- |
| 17 | 30 C., 1 hour | 89 |
| 18 | 30 C., 2 hours | 95 |
| 19 | 30 C., 3 hours | 95 |
| 20 | 60 C., 30 minutes | 96 |

TABLE 3-continued

| Example | Reaction conditions (temperature, time) | Yield (%) |
| --- | --- | --- |
| 21 | 60 C., 1 hour | 97 |
| 22 | 60 C., 2 hours | 97 |
| 23 | 90 C., 30 minutes | 94 |
| 24 | 90 C., 1 hour | 93 |
| 25 | 90 C., 2 hours | 92 |

EXAMPLE 26-32

Synthesis of Hydrazodicarbonamide (HDCA)

Except that each 0.0029 mole of the catalysts shown in the following Table 4 was used instead of NaBr, the reactions were carried out according to the same method of Example 20. After completion of the reaction, unreacted ammonia was removed and the reaction solution was filtered. The yield of water insoluble HDCA was calculated and shown in the following Table 4.

TABLE 4

| Example | The used catalyst | Yield (%) |
| --- | --- | --- |
| 26 | KBr | 93 |
| 27 | KI | 94 |
| 28 | N-bromosuccinimide (NBS) | 94 |
| 29 | HBr | 96 |
| 30 | PBr$_3$ | 97 |
| 31 | ZnBr$_2$ | 95 |
| 32 | CuBr$_2$ | 95 |

EXAMPLE 33-41

Synthesis of Hydrazodicarbonamide (HDCA)

666.7 g of the sodium chlorobiuret salt prepared according to the manufacturing example 3 was added into a 2 L autoclave, and cooled to 10 C while stirring. After adding 600 g (8.8 moles) of 25% aqueous ammonia solution while maintaining the temperature of the reaction solution at 10 C or less, the reactions were carried out by varying the reactor temperatures and the reaction times while vigorously stirring the reaction solutions. After completion of the reactions, unreacted ammonia was removed and the reaction solution were filtered. The yields of water insoluble HDCA were calculated and shown in the following Table 5.

TABLE 5

| Example | Reaction conditions (temperature, time) | Yield (%) |
| --- | --- | --- |
| 33 | 30 C., 1 hour | 88 |
| 34 | 30 C., 2 hours | 95 |
| 35 | 30 C., 3 hours | 96 |
| 36 | 60 C., 30 minutes | 96 |
| 37 | 60 C., 1 hour | 95 |
| 38 | 60 C., 2 hours | 96 |
| 39 | 90 C., 30 minutes | 95 |
| 40 | 90 C., 1 hour | 93 |
| 41 | 90 C., 2 hours | 92 |

EXAMPLE 42-48

Synthesis of Hydrazodicarbonamide (HDCA)

Except that each 0.0029 mole of the catalysts shown in the following Table 6 was used instead of NaBr, the reactions were carried out according to the same method of Example 36. After completion of the reactions, unreacted ammonia was removed and the reaction solutions were filtered. The yields of water insoluble HDCA were calculated and shown in the following Table 6.

TABLE 6

| Example | The used catalyst | Yield (%) |
|---|---|---|
| 42 | KBr | 94 |
| 43 | KI | 94 |
| 44 | N-bromosuccinimide (NBS) | 95 |
| 45 | HBr | 95 |
| 46 | PBr₃ | 96 |
| 47 | ZnBr₂ | 96 |
| 48 | CuBr₂ | 95 |

EXAMPLES 49-53

Synthesis of Hydrazodicarbonamide (HDCA)

593.1 g of the chlorobiuret sodium salt prepared according to the manufacturing example 1 was added into a 2 L autoclave, and cooled to 10□ while stirring. After adding 25% aqueous ammonia solution while varying the amounts thereof as shown in the following Table 7 and maintaining temperature of the reaction solution at 10 C or less, the reactions were carried out at 60 C for 30 minutes while vigorously stirring the reaction solutions. After completion of the reactions, unreacted ammonia was removed and the reaction solutions were filtered. The yields of water insoluble HDCA were shown in the following Table 7.

TABLE 7

| Example | The amount of ammonia used, ammonia/chlorobiuret sodium salt (molar ratio) | Yield (%) |
|---|---|---|
| 49 | 15 | 88 |
| 50 | 20 | 97 |
| 51 | 30 | 98 |
| 52 | 60 | 95 |
| 53 | 90 | 94 |

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for preparing hydrazodicarbonamide comprising the steps of:

obtaining metal monochiorobiuret salt having formula 2 or 3 by reacting a biuret having the formula 1 with a metal hypochloride, or by reacting the biuret having formula 1 with a chlorinating agent and a base; and reacting the obtained metal monochlorobiuret salt with ammonia, wherein the hydrazodicarbonamide is produced in the presence of a catalyst including bromine or iodine atom and generating bromine or iodine ion during the reaction,

(formula 1)

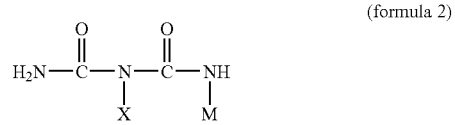

(formula 2)

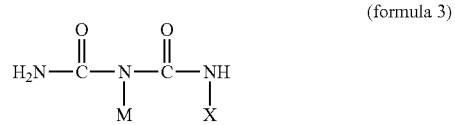

(formula 3)

in the above formulas 2 and 3, M is a metal, and X is a chlorine ion (Cl), wherein the reaction solvent for preparing hydrazodicarbonamide from biuret is a mixture of water and a hydrophobic organic solvent.

2. The method according to claim 1, wherein the hydrophobic organic solvent is selected from the group consisting of a chlorinated hydrocarbon, an aliphatic hydrocarbon, an aromatic hydrocarbon, an acetate, an ether, and mixtures thereof.

3. The method according to claim 1, wherein the metal monochlorobiuret salt is produced by reacting the biuret having formula 1 with a chlorinating agent to obtain a monochlorobiuret having the formula 4 or 5, and by reacting the obtained monochlorobiuret with a base,

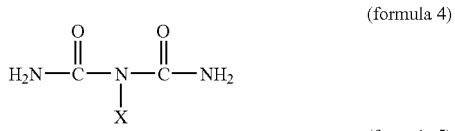

(formula 4)

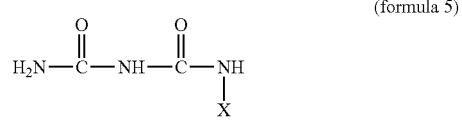

(formula 5)

in the above formulas 4 and 5, X is a chlorine ion (Cl).

4. The method according to claim 3, wherein the reaction of the monochlorobiuret and a base is carried out in the hydrophobic organic solvent separated from water.

5. A method for preparing hydrazodicarbonamide comprising the steps of:

obtaining metal monochiorobiuret salt having formula 2 or 3 by reacting a biuret having the formula 1 with a metal hypochloride, or by reacting the biuret having formula 1 with a chlorinating agent and a base; and reacting the obtained metal monochlorobiuret salt with ammonia, wherein the hydrazodicarbonamide is produced in the presence of a catalyst including bromine or iodine atom and generating bromine or iodine ion during the reaction,

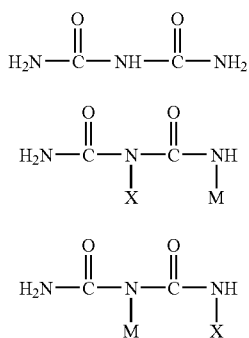

(formula 1)

(formula 2)

(formula 3)

in the above formulas 2 and 3, M is a metal, and X is a chlorine ion (Cl), wherein the reaction solvent for preparing hydrazodicarbonamide from biuret is a mixture of water and a hydrophobic organic solvent selected from the group consisting of a chlorinated hydrocarbon, an aliphatic hydrocarbon, an aromatic hydrocarbon, an acetate, an ether, and mixtures thereof.

6. A method for preparing hydrazodicarbonamide comprising the steps of:

obtaining metal monochlorobiuret salt having formula 2 or 3 by reacting a biuret having the formula 1 with a metal hypochloride, or by reacting the biuret having formula 1 with a chlorinating agent and a base; and reacting the obtained metal monochlorobiuret salt with ammonia in the presence of a catalyst including bromine or iodine atom and generating bromine or iodine ion during the reaction, wherein the bromine or iodine ion replaces the chlorine ion present on the monochlorobiuret,

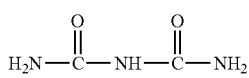

(formula 1)

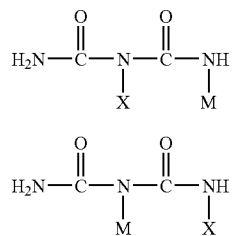

(formula 2)

(formula 3)

in the above formulas 2 and 3, M is a metal, and X is a chlorine ion (Cl), wherein the reaction solvent for preparing hydrazodicarbonamide from biuret is a mixture of water and a second solvent is capable of being separated from water by phase separation.

7. The method according to claim 6, wherein the second solvent is selected from the group consisting of a chlorinated hydrocarbon, an aliphatic hydrocarbon, an aromatic hydrocarbon, an acetate, and mixtures thereof.

8. The method according to claim 6, wherein the metal monochlorobiuret salt is produced by reacting the biuret having formula 1 with a chlorinating agent to obtain a monochlorobiuret having the formula 4 or 5, and by reacting the obtained monochlorobiuret with a base,

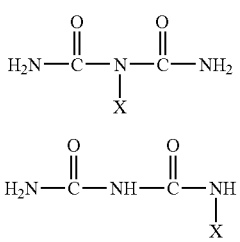

(formula 4)

(formula 5)

in the above formulas 4 and 5, X is a chlorine ion (Cl).

9. The method according to claim 8, wherein the reaction of the monochlorobiuret and a base is carried out in the second solvent separated from water.

* * * * *